United States Patent [19]

McFerran et al.

[11] Patent Number: 5,472,880
[45] Date of Patent: Dec. 5, 1995

[54] CONDUCTANCE MEASUREMENTS IN ORGANIC SOLVENTS

[75] Inventors: Neil V. McFerran; Brian Walker, both of Belfast, Northern Ireland; Donald T. Elmore, Oxford, United Kingdom

[73] Assignee: The Queen's University of Belfast, Belfast, Northern Ireland

[21] Appl. No.: 317,282

[22] Filed: Oct. 3, 1994

Related U.S. Application Data

[63] Continuation of Ser. No. 85,251, Jun. 29, 1993, abandoned, which is a continuation of Ser. No. 634,876, Jan. 10, 1991, abandoned.

[30] Foreign Application Priority Data

May 24, 1988 [GB] United Kingdom .................. 8812277

[51] Int. Cl.$^6$ .............................. C07K 1/00; G01N 27/06
[52] U.S. Cl. .............................. 436/86; 436/89; 436/149; 436/150; 422/82.02; 422/82.01
[58] Field of Search ................................ 436/100, 86, 55, 436/89, 150, 163, 149; 422/82.01, 82.02, 82.03; 530/333, 334, 300

[56] References Cited

U.S. PATENT DOCUMENTS

| | | | |
|---|---|---|---|
| 3,468,764 | 9/1969 | Cohen et al. | 204/1 |
| 4,581,167 | 4/1986 | Carpino et al. | 260/112.5 R |
| 4,701,304 | 10/1987 | Horn et al. | 422/62 |
| 4,746,490 | 5/1988 | Saneii | 436/89 |
| 4,755,558 | 7/1988 | Kalbag | 525/54.1 |
| 4,777,019 | 10/1988 | Dandekar | 422/68 |
| 4,800,166 | 1/1989 | Horn et al. | 436/55 |
| 4,855,486 | 8/1989 | Kalbag | 560/158 |

FOREIGN PATENT DOCUMENTS 9011291 10/1990 WIPO.

*Primary Examiner*—James C. Housel
*Assistant Examiner*—Long V. Le
*Attorney, Agent, or Firm*—Salter & Michaelson

[57] ABSTRACT

A method for quantitatively measuring an acid in a polar organic solvent involves adding a sterically hindered base, such as diisopropylentylamine, triethylamine or N-methylmorpholine to the solvent and measuring the conductance of the mixture. The method has particular relevance in monitoring the progress of preactivation, coupling and deprotection reactions in solid phase peptide synthesis (SPPS).

16 Claims, 2 Drawing Sheets

CONDUCTANCE MEASUREMENTS IN ORGANIC SOLVENTS

This is a continuation of application Ser. No. 08/085,251, filed Jun. 29, 1993, abandoned, which is a continuation of application Ser. No. 07/634,876 filed Jan. 10, 1991, abandoned.

BACKGROUND OF THE INVENTION

This invention relates to quantitative measurement of acids in polar organic solvents and also to the application of such measurements for performance control.

One application of the invention is to solid phase peptide synthesis.

To maximise the efficiency of solid phase peptide synthesis in an automated system the extent of progress of each stage of the process must be estimated by a reliable and sensitive monitoring procedure. Data obtained in this way may be used to form the basis of decision making structures in a synthesis instrument capable of monitoring its own performance and modifying its synthetic approach on the basis of its experience of past syntheses. The monitoring system is central to this enhanced performance.

On-line monitoring in solid phase peptide synthesis has been achieved in certain cases by the use of chromogenic reagents whose reaction may be detected by the use of a dedicated spectrophotometer (Dryland A. & Sheppard, R. C. 1986, J.Chem. Soc. Perkin Trans. I. 125–137, Cameron, L. Meldahl, M. & Sheppard R. C. 1987 J.Chem. Soc.Chem. Commun, pp 270–272). This approach leads to a significant cost increase both in capital outlay for the instrumentation and also in running costs in terms of the specialised reagents to allow this on-line monitoring. Commercial instruments using this technology are available (Pharmacia/LKB Biolynx 4170, Milligen Series 9000), but no direct use is made of the available data in this instrument. In addition this form of monitoring only permits the use of one of the two current chemical process technologies for the coupling (that based on the fluorenylmethoxycarbonyl, Fmoc, protecting group for the incoming amino acid). The use of Fmoc as a protecting group has not received universal acceptance. The alternative currently available protecting group tertiary butoxy carbonyl, t Boc may not be used.

The present invention has been made from a consideration of this problem.

SUMMARY OF THE INVENTION

According to the invention there is provided a method for quantitative measurement of an acid in polar organic solvent comprising adding a sterically hindered base to the solvent and measuring the conductance of the mixture.

Figure 2:
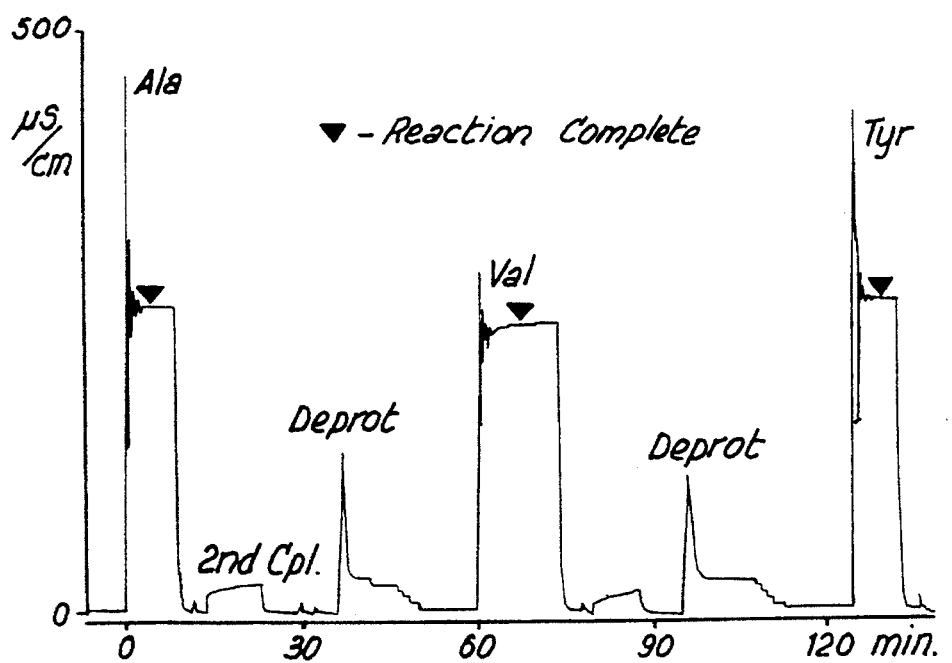
FIGS. 2 and 3 show the conductance profiles of normal (two-fold) molar excess of pentafluorophenyl ester over free resin-bound amino groups.
Figure 3:
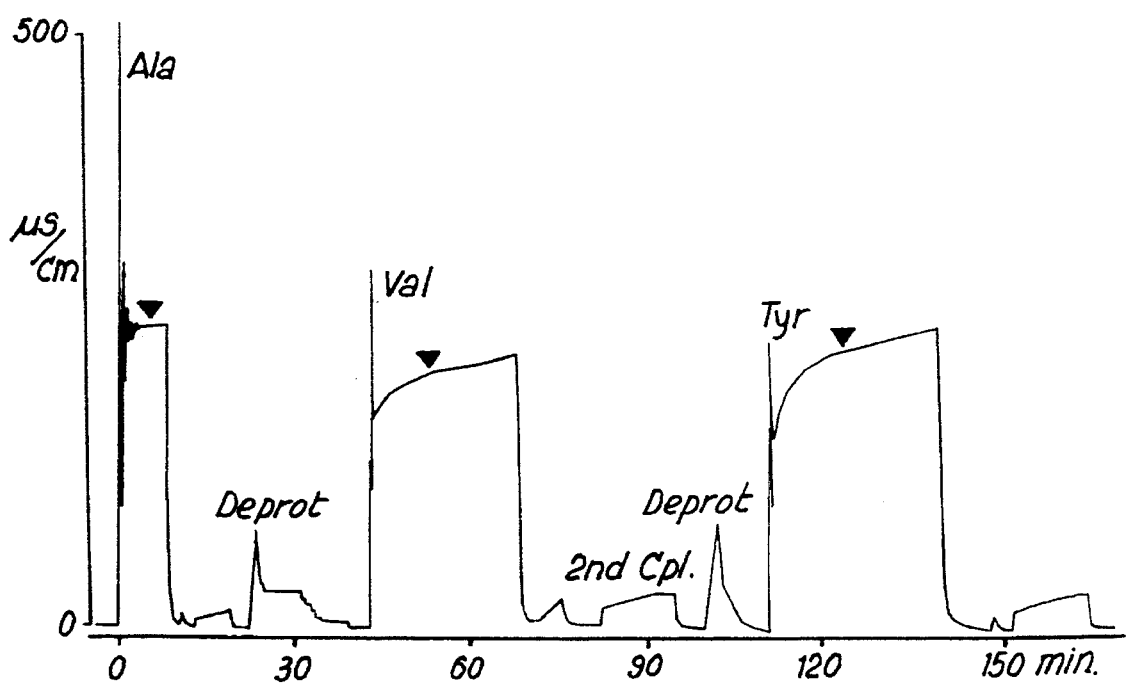

More specifically:

FIG. 2 shows sequential coupling of alanine, valine, and tyrosine as pentafluorophenyl esters to $H_2N$-Leu-O-Resin; and FIG. 3 shows sequential coupling of alanine, valine and tyrosine as pentafluorophenyl esters to $H_2N$-Leu-Tyr-Val-Ala-Leu-O-Resin.

DESCRIPTION OF THE PREFERRED EMBODIMENTS

The use of conductance measurements of the solution surrounding the support in solid phase peptide synthesis offers a universal means of monitoring the progress of coupling and deprotection reactions with both chemistries and thus has much wider appeal than existing optical techniques. It also offers the potential for monitoring the formation of activated species prior to the coupling reaction, and their stability during the coupling period. The conductance measurements used to quantitate acid release (in the coupling or deprotection reactions) or its consumption (in activation reactions) are preferably made using inert electrodes with polarity alternating at frequencies between 70 and 5,000,000 Hz. In solid phase peptide synthesis free acids are liberated after the activated amino acid reacts with the growing peptide on the support regardless of the means used to activate the amino acid (either symmetrical anhydrides or activated esters may be used for this purpose).

As solid phase synthesis is carried out in non-ionising solvents (such as dimethylformamide, dichloromethane, dimethylacetamide, N-methylpyrrolidone, dimethylsulphoxide or methanol) these acids liberated during coupling are not ionised and cannot be used to indicate the extent of the coupling reaction conductometrically without the addition of a base to induce ionisation. In this connection, the base reacts with the free acids to form a conjugate acid of the base which can be conductimetrically measured. A quantitative measurement of the free acid can then be determined from the measurement of the conjugate acid. It is pointed out however, that this base must be sterically hindered from reacting with the Fmoc protecting group. Examples of bases that can be used in the invention include diisopropylethylamine, triethylamine, pyridine and N-methylmorpholine. The preferred amount of base added to the solvent is in the range from 0.1 to 10% by volume. The inclusion of the base allows conductance measurements to be carried out with only small differences in quantitation sensitivity in the range 5–100 mM acid, (the normal range of concentrations encountered in solid phase syntheses).

To form the activated species prior to coupling, a protected amino acid is converted to either a protected symmetrical anhydride or to a protected activated ester. The extent of this reaction may be monitored by following the reduction in base-mediated conductance associated with the formation of the activated species and concomitant loss of free protected amino acid.

In the coupling step of solid phase peptide synthesis free acids are liberated during reaction of the activated amino acid with the growing peptide on the support. Regardless of the means used to activate the incoming amino acid this free acid generates a rise in base-mediated conductance which will be directly related to the extent of the coupling at all times during the reaction. Either symmetrical anhydrides or activated esters may be used to activate the incoming amino acid.

The complementary step to coupling is deprotection to allow addition of the next residue to the growing peptide. Base-mediated conductance measurements also offer a means of monitoring this reaction with both protection regimes. In the case of tBoc chemistry the normal strategy calls for the tertiarybutoxycarbonyl group to be removed by excess acid such as trifluoroacetic acid. A proportion of the excess acid is quantitatively bound to the terminal amino groups of the resin-bound peptide through ionic interactions. On addition of base the trifluoroacetate ions are quantitatively displaced from the peptide, giving rise to a conductance signal whose extent is directly related to the quantity of free amino groups present on the peptide. A similar effect has been observed during deprotection using Fmoc chemistry.

Conductance measurements in the presence of sterically hindered base enables a significant increase in coupling efficiency to be achieved through the speed of response and reliability of a detector generating sufficient data to allow the instrument to make informed decisions on the best coupling strategy to be adopted at each stage in the synthesis. This may be achieved at minimal extra capital cost and barely detectable increase in running costs.

Illustrative examples of base-potentiated conductometric signals derived from the presence of acid in polar solvents are shown below. These are accompanied by conductance traces from typical solid phase peptide synthesis reactions carried out in a continuous flow reactor at 25° C. using dimethylformamide as solvent with 0.5% diisopropylethylamine (v/v) added to potentiate the conductance signals.

An index of the designation used in the Examples is as follows:

| | |
|---|---|
| DMA | dimethyl acetamide |
| DMF | dimethylformamide |
| DCM | dichloromethane |
| DIPEA | diisopropylethylamine |
| TEA | triethylamine |
| NMM | N-methylmorpholine |
| PFPOH | pentafluorophenol |
| TFA | Trifluoroacetic acid |

EXAMPLES

1 Calibration Curves 1.1 Calibration curves for use with Fmoc chemistry
  1.1.1 for PFPOH-ester mediated Synthesis
    1.1.1.1 using 5.0% DIPEA in DMF (v/v).
    1.1.1.2 using 0.5% DIPEA in DMF (v/v).
    1.1.1.3 using 5.0% DIPEA in DMA (v/v).
    1.1.1.4 using 4.0% TEA in DMF (v/v).
    1.1.1.5 using 3.2% N-MM in DMF (v/v).
  1.1.2 for symmetrical anhydride mediated Synthesis
    1.1.2.1 using Fmoc alanine in 0.5% DIPEA/DMF (v/v).
    1.1.2.2 using Fmoc isoleucine in 0.5% DIPEA/DMF (v/v).
1.2 Calibration Curves for use with tBoc chemistry
  1.2.1 for PFPOH-ester mediated Synthesis
    1.2.1.1 using 5.0% DIPEA in DCM/DMF (1:1 v/v).
    1.2.1.2 using 0.5% DIPEA in DCM/DMF (1:1 v/v).
  1.2.2 for symmetrical anhydride mediated Synthesis
    1.2.2.1 using Fmoc alanine in 0.5% DIPEA in DCM/DMF (1.1 (v/v)).
  1.2.3 for TFA (deprotection monitoring)
    1.2.3.1 using 0.5% DIPEA in DMC/DMF (1:1 v/v).

2 Reaction Profiles 2.1 Sequential sub-equivalent Reactions
2.2 Normal Reaction profiles (two-fold molar excess)

All conductance measurements were carried out at 25° C. using a Radiometer conductance meter (type CDM 83) with a pair of platinum electrodes (cell constant 0.807 cm$^{-1}$). A Pharmacia chart recorder was used to record the CDM 83 output during complete reaction/deprotection cycles of peptide synthesis.

1 Calibration Curves 1.1.1.1 Calibration Curve for use in PFPOH-ester mediated Synthesis, 5.0% DIPEA in DMF (v/v)—for Fmoc chemistry.

| [PFPOH] mM | Conductance uS/cm |
|---|---|
| 0.0 | 3.88 |
| 1.0 | 38.0 |
| 2.0 | 50.7 |
| 3.0 | 68.0 |
| 4.0 | 73.2 |
| 5.0 | 89.0 |
| 6.0 | 100.4 |
| 7.0 | 115.0 |
| 8.0 | 118.6 |
| 9.0 | 147.0 |
| 10.0 | 148.0 |
| 11.0 | 149.5 |
| 13.0 | 165.5 |
| 15.0 | 175.5 |
| 17.0 | 191.5 |
| 19.0 | 207.0 |
| 20.0 | 215.5 |

Conductance of solutions of PFPOH (20mM) in DMF containing varying amounts of DIPEA.

| [DIPEA] % (v/v) | Conductance uS/cm |
|---|---|
| 0.0 | 5.0 |
| 0.05 | 82.0 |
| 0.10 | 127.0 |
| 0.50 | 287.0 |
| 5.00 | 219.0 |

1.1.1.2 Calibration Curve for use in PFPOH-ester mediated Synthesis, 0.5% DIPEA in DMF (v/v)—for Fmoc chemistry.

| [PFPOH] mM | Conductance uS/cm |
|---|---|
| 0.0 | 1.9 |
| 2.0 | 60.4 |
| 4.0 | 85.5 |
| 6.0 | 112.4 |
| 8.0 | 133.0 |
| 10.0 | 167.0 |
| 14.0 | 221.0 |
| 16.0 | 263.0 |
| 18.0 | 278.0 |
| 20.0 | 292.0 |

1.1.1.3 Calibration Curve for use in PFPOH-ester mediated Synthesis, 5.0% DIPEA in DMA (v/v)—for Fmoc chemistry.

| [PFPOH] mM | Conductance uS/cm |
|---|---|
| 0.0 | 0.0(10.4) |
| 2.0 | 29.9 |
| 4.0 | 56.1 |
| 6.0 | 72.4 |
| 8.0 | 93.9 |
| 10.0 | 112.9 |
| 12.0 | 124.6 |
| 14.0 | 138.6 |
| 16.0 | 154.6 |
| 18.0 | 168.6 |
| 20.0 | 183.6 |

1.1.1.4 Calibration Curve for use in PFPOH-ester mediated Synthesis, using 4.0% TEA in DMF (v/v)—for Fmoc chemistry.

| [PFPOH] mM | Conductance uS/cm |
|---|---|
| 0.0 | 0.0(3.09) |
| 5.0 | 77.9 |
| 10.0 | 114.2 |
| 15.0 | 146.9 |
| 20.0 | 175.9 |

Calibration Curves for Fmoc chemistry 1.1.1.5 Calibration Curve for use in PFPOH-ester mediated Synthesis, using 3.2% N-MM in DMF (v/v)—for Fmoc chemistry.

| [PFPOH] mM | Conductance uS/cm |
|---|---|
| 0.0 | 0.0(2.28) |
| 5.0 | 63.8 |
| 10.0 | 102.7 |
| 15.0 | 149.7 |
| 20.0 | 185.7 |

1.1.2.1 Calibration Curve for symmetrical anhydride mediated Synthesis, using 0.5% DIPEA in DMF (v/v)—Fmoc chemistry.

| [Fmoc alanine] mM | Conductance uS/cm |
|---|---|
| 0.0 | 0.0(3.0) |
| 5.0 | 18.0 |
| 10.0 | 34.0 |
| 15.0 | 48.0 |
| 20.0 | 65.0 |
| 30.0 | 83.0 |
| 40.0 | 107.0 |
| 50.0 | 132.0 |

1.1.2.2 Calibration Curve for symmetrical anhydride mediated Synthesis, using 0.5% DIPEA in DMF (v/v)—Fmoc chemistry.

| [Fmoc isoleucine] mM | Conductance uS/cm |
|---|---|
| 0.0 | 0.0(3.0) |
| 5.0 | 21.0 |
| 10.0 | 34.0 |
| 15.0 | 47.0 |
| 20.0 | 63.0 |
| 30.0 | 79.0 |
| 40.0 | 100.0 |
| 50.0 | 128.0 |

1.2.1.1 Calibration Curve for use in PFPOH-ester mediated Synthesis, using 5.0% DIPEA in DCM/DMF (1:1 v/v)—tBocChemisty

| [PFPOH] mM | Conductance uS/cm |
|---|---|
| 0.0 | 0.0(3.8) |
| 2.5 | 35.3 |
| 5.0 | 46.3 |
| 7.5 | 59.9 |
| 10.0 | 66.3 |
| 12.5 | 83.9 |
| 15.0 | 96.2 |
| 17.5 | 109.2 |
| 20.0 | 121.6 |

1.2.1.2 Calibration Curve for use in PFPOH-ester mediated Synthesis, using 0.5% DIPEA in DCM/DMF (1:1 v/v)—tBoc.

| [PFPOH] mM | Conductance uS/cm |
|---|---|
| 0.0 | 0.0(2.0) |
| 2.5 | 32.0 |
| 5.0 | 59.0 |
| 7.5 | 85.0 |
| 10.0 | 89.0 |
| 12.5 | 113.0 |
| 15.0 | 134.0 |
| 17.5 | 172.0 |
| 20.0 | 191.0 |

1.2.2.1 Calibration Curve for symmetrical anhydride mediated Synthesis, using 0.5% DIPEA in DCM/DMF (1:1 v/v)—tBoc.

| [Fmoc alanine] mM | Conductance uS/cm |
|---|---|
| 0.0 | 0.0(3.0) |
| 10.0 | 30.0 |
| 20.0 | 51.0 |
| 30.0 | 75.0 |
| 40.0 | 98.0 |
| 50.0 | 113.0 |

1.2.3.1 Calibration Curve for deprotection monitoring in tBoc syntheses, (all activation technologies). TFA conductance using 0.5% DIPEA in DCM/DMF (1:1 v/v).

| [TFA] mM | Conductance uS/cm |
|---|---|
| 0.0 | 0.0(3.0) |
| 2.5 | 87.0 |
| 5.0 | 123.0 |
| 10.0 | 198.0 |
| 15.0 | 275.0 |
| 20.0 | 328.0 |

2 Reaction Profiles

Figure 1:
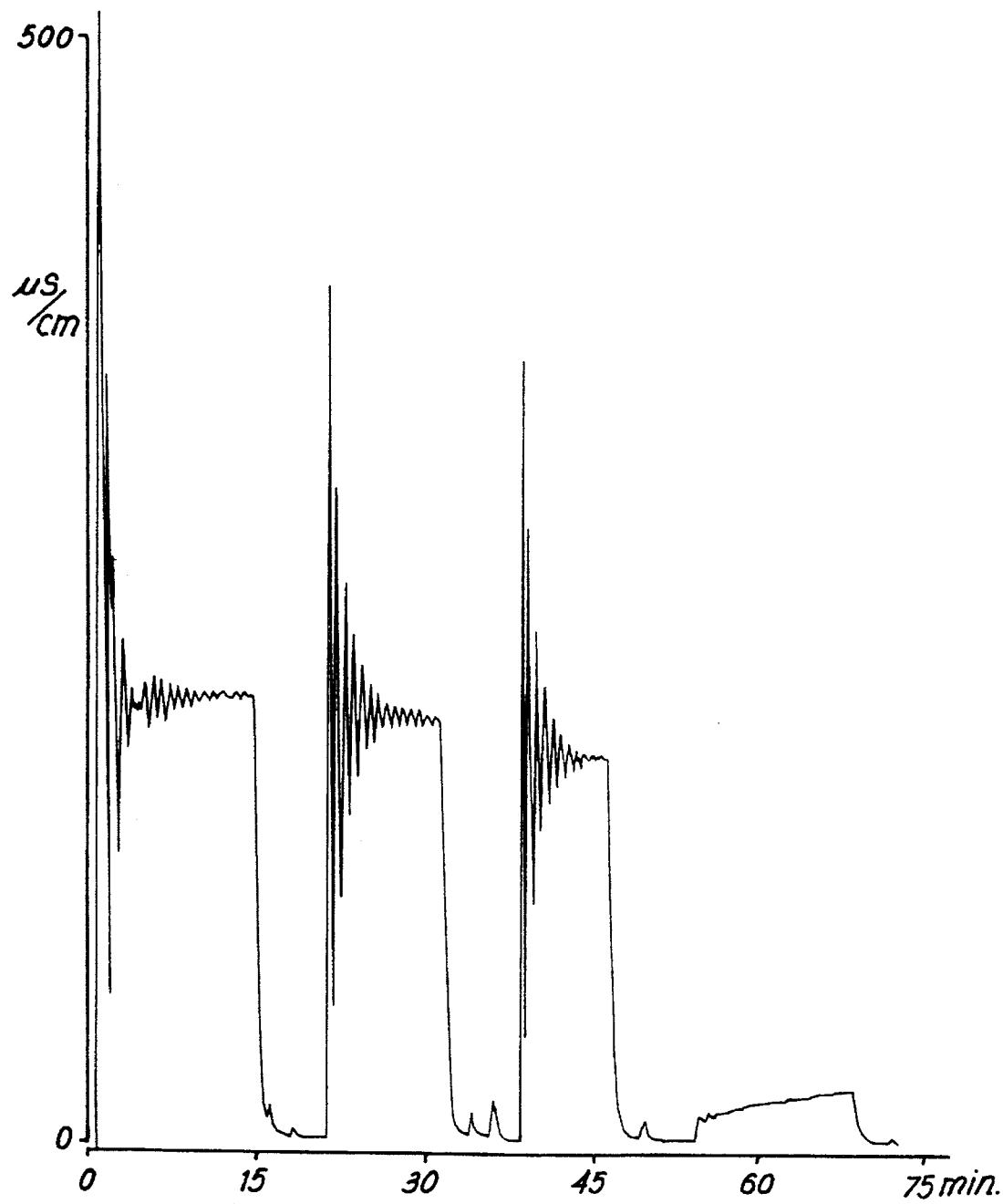
FIG. 1 shows the conductance profiles during reaction of sub-equivalent amounts of FMOC-glycine pentafluorophenyl ester with $H_2N$-Ile-Trp-Ile-Leu-O-Resin.

Referring to the figures it can be seen from FIG. 1 that there is a significant decrease in the extent of reaction on addition of the fourth aliquot (excess) of active ester.

The sequential couplings of FIGS. 2 and 3 indicate that conductance may be used to show that different couplings proceed at different rates, which may be related both to differences in the residue being coupled ($Ala_2>Val_3$) and also to increasing chain-length of the peptide ($Tyr_4>Tyr_8$).

This information allows the default minimum coupling time (10 min) to be extended to accommodate the slower reactions (see $Val_3$ vs. $Val_7$). Again, as in FIG. 1, presentation of excess of the activated species in second couplings gives no significant further reaction, any increase in conductance reflecting reagent instability.

Deprotection may be monitored by an upward transient of the conductance signal, whose width may be taken as an indicator of potential difficulties in the next coupling cycle (eg $Tyr_8$) and whose area is a measure of the number of free amino groups generated during the deprotection process.

We claim:

1. A method for quantitative measurement of free acids released into or removed from a polar organic solvent during a solid phase peptide synthesis reaction, said method consisting essentially of the steps of:
    adding a sterically hindered base to the solvent to form a solution comprising said solvent, said free acids and said base, said base inducing ionization of said free acids; and
    measuring a conductance of the solution to quantitatively measure said ionized free acids, whereby a quantitative measurement of said free acids is determined.

2. A method for quantitative measurement of an acid as claimed in claim 1, wherein the sterically hindered base comprises an amine.

3. A method for quantitative measurement of an acid as claimed in claim 1, wherein the sterically hindered base is selected from a group consisting of: diisopropylethylamine, triethylamine, pyridine, N-methylmorpholine and mixtures thereof.

4. A method for quantitative measurement of an acid as claimed in claim 1 wherein the sterically hindered base is added to the solvent in an amount in the range from 0.1 to 10 percent by volume.

5. A method for quantitative measurement of an acid as claimed in claim 2, wherein the polar organic solvent is selected from a group consisting of: amide, alkane alcohol, other aprotic solvents and mixtures thereof.

6. A method for quantitative measurement of an acid as claimed in claim 5, wherein the solvent is selected from a group consisting of: dimethylformamide, dichloromethane, dimethylacetamide, N-methylpyrrolidone, dimethylsulphoxide, methanol, and mixtures thereof.

7. A method for quantitative measurement of an acid as claimed in claim 2 wherein the conductance of the solution is measured using inert electrodes with polarity alternating at frequencies between 70 and 5,000,000 Hz.

8. A method for quantitative measurement of an acid as claimed in claim 2 wherein progress of preactivation, coupling and deprotection reactions in solid phase peptide synthesis are monitored.

9. A method for quantitative measurement of an acid released into or removed from a polar organic solvent during a solid phase peptide synthesis reaction consisting essentially of the steps of:
    adding a sterically hindered base to the solvent to form a solution comprising said solvent, said acid, and said base, said sterically hindered base reacting in said solvent to induce ionization of said acid; and
    measuring a conductance of the solution to quantitatively measure said ionized acid, whereby a quantitative measurement of said acid is determined.

10. A method for quantitative measurement of an acid as claimed in claim 9, wherein the sterically hindered base comprises an amine.

11. A method for quantitative measurement of an acid as claimed in claim 9, wherein the sterically hindered base is selected from a group consisting of: diisopropylethylamine, triethylamine, pyridine, N-methylmorpholine and mixtures thereof.

12. A method for quantitative measurement of an acid as claimed in claim 9 wherein the sterically hindered base is added to the solvent in an amount in the range from 0.1 to 10 percent by volume.

13. A method for quantitative measurement of an acid as claimed in claim 10, wherein the polar organic solvent is selected from a group consisting of: amide, alkane alcohol, other aprotic solvents and mixtures thereof.

14. A method for quantitative measurement of an acid as claimed in claim 13, wherein the solvent is selected from a group consisting of: dimethylformamide, dichloromethane, dimethylacetamide, N-methylpyrrolidone, dimethylsulphoxide, methanol, and mixtures thereof.

15. A method for quantitative measurement of an acid as claimed in claim 10 wherein the conductance of the solution is measured using inert electrodes with polarity alternating at frequencies between 70 and 5,000,000 Hz.

16. A method for quantitative measurement of an acid as claimed in claim 10 wherein progress of preactivation, coupling and deprotection reactions in solid phase peptide synthesis are monitored.

* * * * *